US012674801B2

(12) United States Patent
Wakayama et al.

(10) Patent No.: US 12,674,801 B2
(45) Date of Patent: Jul. 7, 2026

(54) BIOCHIP AND DETECTION METHOD

(71) Applicant: Toray Industries, Inc., Tokyo (JP)

(72) Inventors: Sho Wakayama, Kamakura (JP); Yoichiro Koshi, Kamakura (JP); Takeshi Baba, Kamakura (JP); Tomonori Kawakami, Kamakura (JP); Masateru Ito, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 1108 days.

(21) Appl. No.: 17/771,884

(22) PCT Filed: Oct. 29, 2020

(86) PCT No.: PCT/JP2020/040595
§ 371 (c)(1),
(2) Date: Apr. 26, 2022

(87) PCT Pub. No.: WO2021/085526
PCT Pub. Date: May 6, 2021

(65) Prior Publication Data

US 2022/0390444 A1 Dec. 8, 2022

(30) Foreign Application Priority Data

Oct. 31, 2019 (JP) ................................ 2019-198466
Nov. 15, 2019 (JP) ................................ 2019-206942

(51) Int. Cl.
*C12Q 1/00* (2006.01)
*C12Q 1/6837* (2018.01)
*G01N 33/543* (2006.01)
*G01N 33/68* (2006.01)

(52) U.S. Cl.
CPC ..... *G01N 33/54366* (2013.01); *C12Q 1/6837* (2013.01); *G01N 33/6854* (2013.01)

(58) Field of Classification Search
CPC ................................................ G01N 33/54366
USPC ........................................................... 436/63
See application file for complete search history.

(56) References Cited

U.S. PATENT DOCUMENTS 6,053,939 A 4/2000 Okuda et al.
2011/0152409 A1 6/2011 Nokihara et al.
2014/0187724 A1 7/2014 Komatsu et al.

FOREIGN PATENT DOCUMENTS

EP 0 791 605 A2 8/1997
EP 3505934 A1 * 7/2019 ........... B01J 20/265
JP 2003-175668 A 6/2003
JP 2006-211959 A 8/2006
JP 2015-040729 A 3/2015
JP 2018-034395 A 3/2018
WO 2001/70641 A1 9/2001
WO 2001/70851 A1 9/2001
WO 2010/001876 A1 1/2010
(Continued)

OTHER PUBLICATIONS

International Search Report dated Jan. 19, 2021 in counterpart International Application No. PCT/JP2020/040595.
(Continued)

*Primary Examiner* — Lyle Alexander
*Assistant Examiner* — Emily R. Berkeley
(74) *Attorney, Agent, or Firm* — DLA Piper LLP (US)

(57) ABSTRACT

A biochip is capable of highly sensitively detecting a measurement target substance. The biochip includes a selective-binding substance capable of selectively binding to the measurement target substance, the selective-binding substance being immobilized on a surface of a substrate through a polymer containing a unit represented by Formula (Ia) or (Ib):

(Ia)

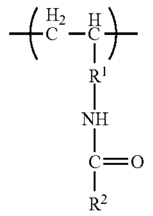

(Ib)

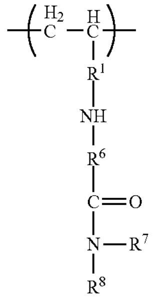

wherein, $R^1$ represents $C_1$-$C_4$ alkylene; $R^2$ represents $R^3$, $OR^4$, or $NHR^5$; $R^3$ and $R^5$ each independently represent a hydrogen atom or $C_1$-$C_4$ alkyl; $R^4$ represents $C_1$-$C_4$ alkyl; $R^6$ represents $C_1$-$C_2$ alkylene; and $R^7$ and $R^8$ each independently represent a hydrogen atom or $C_1$-$C_4$ alkyl.

8 Claims, No Drawings

Specification includes a Sequence Listing.

(56) References Cited

FOREIGN PATENT DOCUMENTS

| | | | |
|---|---|---|---|
| WO | 2010/123039 | A1 | 10/2010 |
| WO | 2013/024694 | A1 | 2/2013 |

OTHER PUBLICATIONS

Written Opinion dated Jan. 19, 2021 in counterpart International Application No. PCT/JP2020/040595.
Extended European Search Report dated Aug. 22, 2023, of counterpart European Patent Application No. 20881001.0.

* cited by examiner

```
SEQUENCE LISTING

<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: Synthetic Polynucleotides, 5'-end amino group

<400> SEQUENCE: 1

aactatacaa cctactacct ca                                          22
```

BIOCHIP AND DETECTION METHOD

TECHNICAL FIELD

This disclosure relates to a biochip comprising a substance ("selective-binding substance") that selectively binds to a measurement target substance, the selective-binding substance being immobilized on a surface of the substrate, and a method of detecting the measurement target substance using the biochip.

BACKGROUND

A biochip comprising a selective-binding substance such as nucleic acid or protein, the selective-binding substance being immobilized on a substrate, is capable of identification of molecules or diagnosis based on a change in the fluorescence intensity and/or the pattern of the fluorescence after selective binding of the selective-binding substance to the measurement target substance and detection of the fluorescence. For accurate identification of molecules and diagnosis by the biochip, the biochip preferably shows a performance that allows highly sensitive detection of the measurement target substance. More specifically, the biochip preferably shows a high signal value and a high signal value/noise value ratio ("SN ratio") upon detection of the fluorescence from the measurement target substance.

Biochips may show variation in the detection sensitivity for the measurement target substance depending on the method of immobilization of the selective-binding substance such as nucleic acid or protein on the substrate. For example, it has been reported that immobilization of a selective-binding substance on a substrate surface through a polymer enables production of a biochip having high detection sensitivity (WO 01/70641 and WO 01/70851). The polymer is often an "amino-group-containing polymer" that contains an amino group in a chemical structure such as polyethyleneimine, polyallylamine, or poly-L-lysine. WO '641 discloses a biochip in which a selective-binding substance is immobilized on a substrate surface through polyethyleneimine, which is an amino-group-containing polymer.

To develop a biochip capable of detection at a high SN ratio, we prepared a biochip by immobilizing a selective-binding substance on a substrate, with reference to WO '641. More specifically, a biochip in which a selective-binding substance is immobilized on a substrate surface through polyethyleneimine, which is an amino-group-containing polymer, was prepared (as mentioned later in Comparative Example 2). As a result, the signal value was improved compared to a biochip in which the selective-binding substance was immobilized on the substrate surface directly by condensation without being mediated by a polymer (as mentioned later in Comparative Example 1), but the noise value also increased so that no improvement in the SN ratio was found. We thus studied immobilization of a selective-binding substance on a substrate through polyallylamine, which is another amino-group-containing polymer (as mentioned later in Comparative Example 3). As a result, the signal value was further improved compared to the biochip in which the selective-binding substance was immobilized through polyethyleneimine, but the noise value also further increased, resulting in insufficient improvement of the SN ratio. Thus, we found that simple immobilization of a selective-binding substance through an amino-group-containing polymer does not necessarily lead to improvement in the signal value and the SN ratio and, hence, there is a need to provide structure of the amino-group-containing polymer to obtain a biochip excellent in both the signal value and the SN ratio.

SUMMARY

We discovered that a biochip that provides a high signal value and a high SN ratio can be obtained by using a polymer whose side-chain structure is modified.

We thus provide (1) to (8):

(1) A biochip comprising a selective-binding substance capable of selectively binding to a measurement target substance, the selective-binding substance being immobilized on a surface of a substrate through a polymer containing a unit represented by Formula (Ia) or (Ib):

(Ia)

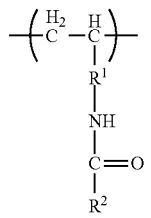

(Ib)

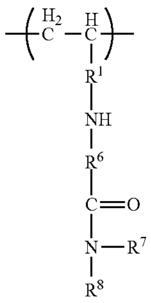

wherein in Formulae (Ia) and (Ib), $R^1$ represents $C_1$-$C_4$ alkylene; $R^2$ represents $R^3$, $OR^4$, or $NHR^5$; $R^3$ and $R^5$ each independently represent a hydrogen atom or $C_1$-$C_4$ alkyl; $R^4$ represents $C_1$-$C_4$ alkyl; $R^6$ represents $C_1$-$C_2$ alkylene; and $R^7$ and $R^8$ each independently represent a hydrogen atom or $C_1$-$C_4$ alkyl.

(2) The biochip according to (1), wherein the polymer is represented by the Formula (Ia) (wherein $R^1$ and $R^2$ have the same definitions as recited in (1)).

(3) The biochip according to (1), wherein the polymer is represented by the Formula (Ib) (wherein $R^6$, $R^7$, and $R^8$ have the same definitions as recited in (1)).

(4) The biochip according to any one of (1) to (3), wherein the polymer is a heteropolymer.

(5) The biochip according to (4), wherein the heteropolymer is a heteropolymer comprising a unit represented by Formula (II):

(II)

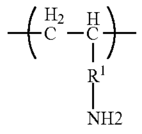

wherein $R^1$ represents $C_1$-$C_4$ alkylene.

(6) The biochip according to any one of (1) to (5), wherein the polymer has a number average molecular weight of 300 to 1,000,000.

(7) The biochip according to any one of (1) to (6), wherein the selective-binding substance is a nucleic acid or a protein.

(8) A method of detecting a measurement target substance using the biochip according to any one of (1) to (7), the biochip comprising a selective-binding substance capable of selectively binding to the measurement target substance, the selective-binding substance being immobilized on a surface of a substrate, the method comprising the steps of: bringing a specimen containing the measurement target substance into contact with the surface of the substrate, to allow formation of a complex with the selective-binding substance; and detecting the complex.

A biochip capable of highly sensitively detecting a measurement target substance can be provided by immobilizing a selective-binding substance on a substrate through a polymer containing a unit represented by Formula (Ia) or (Ib), especially through a heteropolymer containing a unit represented by Formula (Ia) or (Ib) and a unit represented by Formula (II). By using the biochip, more accurate identification of molecules and diagnosis are possible.

DETAILED DESCRIPTION

Our biochip comprises a selective-binding substance to a measurement target substance, the selective-binding substance being immobilized on a surface of a substrate through a polymer containing a unit represented by Formula (Ia) or (Ib).

In Formulae (Ia) and (Ib), $R^1$ represents $C_1$-$C_4$ alkylene. $R^1$ is preferably a methylene group, which has one carbon atom, or an ethylene group, which has two carbon atoms. A methylene group, which has one carbon atom, is more preferred.

In Formula (Ia), $R^2$ represents $R^3$, $OR^4$, or $NHR^5$. $R^3$ and $R^5$ each independently represent a hydrogen atom or $C_1$-$C_4$ alkyl, and $R^4$ represents $C_1$-$C_4$ alkyl. $R^3$ is preferably a methyl group, which has one carbon atom, or an ethyl group, which has two carbon atoms. A methyl group, which has one carbon atom, is more preferred. $R^4$ is preferably a methyl group, which has one carbon atom, or an ethyl group, which has two carbon atoms. A methyl group, which has one carbon atom, is more preferred. $R^5$ is preferably a hydrogen atom.

In Formula (Ib), $R^6$ represents $C_1$-$C_2$ alkylene. $R^6$ is preferably an ethylene group, which has two carbon atoms.

In Formula (Ib), $R^7$ and $R^8$ each independently represent a hydrogen atom or $C_1$-$C_4$ alkyl. Each of $R^7$ and $R^8$ is preferably a hydrogen atom or a methyl group, which has one carbon atom, more preferably a hydrogen group.

The polymer is not limited as long as it contains a unit represented by Formula (Ia) or (Ib). It may also be a heteropolymer also containing a unit other than the unit represented by Formula (Ia) or (Ib). When the polymer is a heteropolymer to be covalently immobilized on the substrate surface, the unit other than the unit represented by Formula (Ia) or (Ib) preferably contains a reactive functional group. Examples of the reactive functional group include amino, carboxyl, hydroxy, halogeno, tosyl, epoxy, acyl, and azide. The reactive functional group is preferably amino. When the polymer is a heteropolymer, the ratio of units represented by Formula (Ia) or (Ib) (collectively referred to as Formula (I) for convenience) to the total units is preferably 5 mol % to 95 mol %, more preferably 10 mol % to 90 mol %, still more preferably 30 mol % to 70 mol %.

When the polymer containing a unit represented by Formula (Ia) or (Ib) is a heteropolymer, it is preferably a heteropolymer containing a unit represented by Formula (II). In Formula (II), $R^1$ represents $C_1$-$C_4$ alkylene similarly to $R^1$ in Formula (Ia) or (Ib). The ratio of units represented by Formula (I) to the total of units represented by Formula (I) and units represented by Formula (II) ((m/(m+n) described later) in the heteropolymer is preferably 5 mol % to 95 mol %, more preferably 10 mol % to 90 mol %, still more preferably 30 mol % to 70 mol %.

Examples of the method of producing the polymer containing the unit represented by Formula (I) include: a method (A) in which a monomer represented by Formula (III) as a raw material is polymerized, and then their side-chain amino groups are modified; and a method (B) in which a monomer represented by Formula (III) are similarly used as a raw material, but their side-chain amino groups are modified before the polymerization; as shown in the following schemes. The former method (A) is preferred.

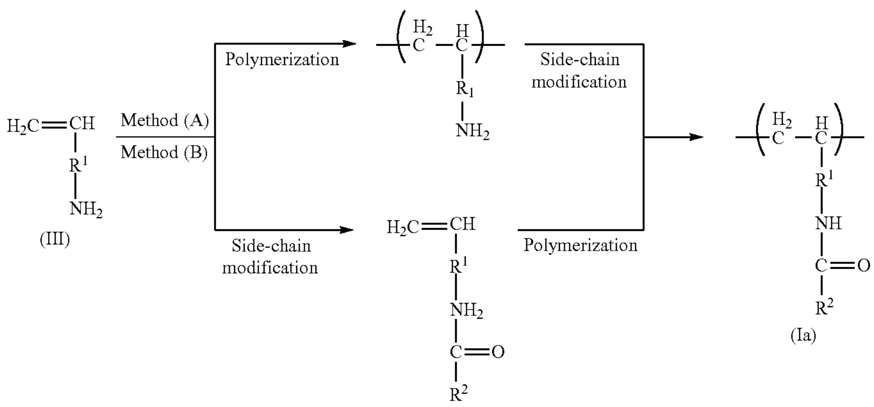

-continued

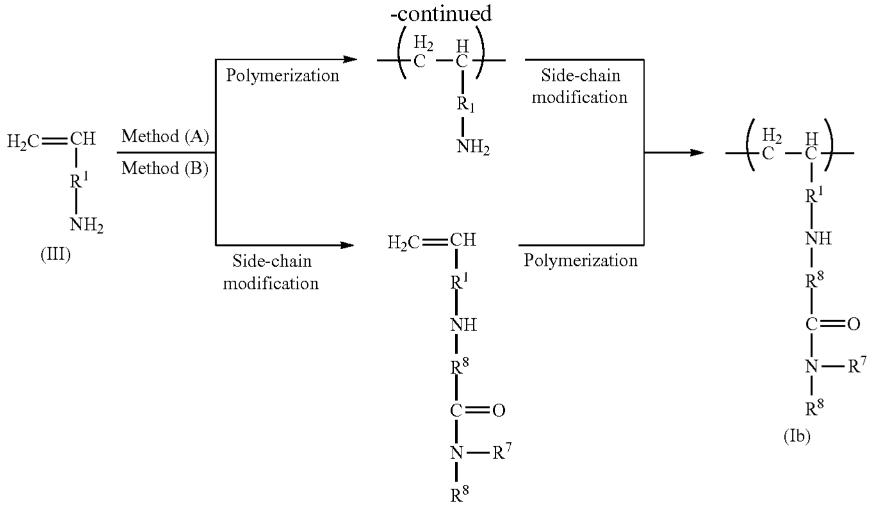

(III)

(Ib)

In Formula (III), $R^1$ represents $C_1$-$C_4$ alkylene similarly to $R^1$ in Formulae (Ia) and (Ib). The monomer represented by Formula (III) is available from reagent manufacturers (such as Merck or Enamine).

Polymerization of the monomer represented by Formula (III) in the method (A) may be carried out by radical polymerization. For example, to 10 to 80% by weight monomer solution, an azo radical polymerization initiator (such as 2,2'-azobis(2-amidinopropane) dihydrochloride) may be added at 0.1 to 30 mol % with respect to the monomer, and the resulting mixture may be reacted under conditions at room temperature to 80° C. for 3 to 100 hours. A homopolymer of a monomer in which $R^1$ in Formula (III) is a methylene group, which has one carbon atom, is available from reagent manufacturers (such as Nittobo Medical Co., Ltd.).

Examples of the method of modification of side-chain amino groups after the polymerization of the monomer represented by Formula (III) include a method in which reaction with a reagent for amino-group modification is carried out as follows.

When $R^2$ in Formula (Ia) is $R^3$, and the $R^3$ is a hydrogen atom, a formylation reagent such as 1-formylpiperidine may be used as the reagent for amino-group modification. When the $R^3$ is $C_1$-$C_4$ alkyl, an acid anhydride ($R^3CO_2COR^3$) such as acetic anhydride, propionic anhydride, butyric anhydride, or valeric anhydride may be used as the reagent for amino-group modification.

When $R^2$ in Formula (Ia) is $OR^4$, a diester carbonate ($R^4OCO_2R^4$) such as dimethyl carbonate, diethyl carbonate, dipropyl carbonate, or dibutyl carbonate may be used as the reagent for amino-group modification.

When $R^2$ in Formula (Ia) is $NHR^5$, an isocyanate derivative ($R^5$—NCO) may be used as the reagent for amino-group modification.

When $R^6$ in Formula (Ib) is a methylene group, which has one carbon atom, a bromoacetamide derivative ($BrCH_2CONR^7R^8$) such as 2-bromoacetamide, 2-bromo-N-methylacetamide, 2-bromo-N-ethylacetamide, 2-bromo-N-propylacetamide, 2-bromo-N-isopropylacetamide, 2-bromo-N-butylacetamide, 2-bromo-N,N-dimethylacetamide, or 2-bromo-N,N-diethylacetamide may be used as the reagent for amino-group modification.

When $R^6$ in Formula (Ib) is an ethylene group, which has two carbon atoms, an acrylamide derivative ($CH_2$═$CHCONR^7R^8$) such as acrylamide, N-methylacrylamide, N-ethylacryl-amide, N-propylacrylamide, N-isopropylacrylamide, N-butylacrylamide, N,N-dimethylacrylamide, or N,N-diethylacrylamide may be used as the reagent for amino-group modification.

The reaction of the reagent for amino-group modification with the polymer of the monomers represented by Formula (III) may be carried out by, for example, adding the reagent for amino-group modification to 10 to 50% by weight polymer solution, and allowing the reaction to proceed under conditions at room temperature to 80° C. for 3 to 100 hours.

The side-chain modification of the monomer represented by Formula (III) in the method (B) may be carried out using a reagent for amino-group modification in the same manner as described above. The polymerization of the modified monomer may also be carried out under the same general conditions as described above.

The heteropolymer containing a unit represented by Formula (Ia) or (Ib) and a unit represented by Formula (II) may be produced by modifying only a part of the side-chain amino groups in the step of modification of the side-chain amino groups. In particular, it is preferred to employ the method (A) described above such that only a part of the side-chain amino groups of the polymer of the monomers represented by Formula (III) is modified. In this example, the ratio between the units represented by Formula (Ia) or (Ib) and the units represented by Formula (II) may be controlled by adjusting the molar ratio between the side-chain amino groups in the polymer and the reagent for amino-group modification employed. The ratio between the units represented by Formula (Ia) or (Ib) and the units represented by Formula (II) can be calculated by $^1$H-NMR measurement.

The molecular weight of the polymer in the biochip in terms of the number average molecular weight is preferably 300 to 1,000,000, more preferably 1000 to 100,000, still more preferably 1600 to 25,000. The molecular weight of the polymer can be calculated by, for example, the gel permeation chromatography (GPC) method using polyethylene glycol as a standard sample.

The material of the substrate of the biochip may be any of a resin, glass, metal, and silicon wafer. From the viewpoint of simplicity of surface treatment and mass production, the material is preferably a resin.

Examples of the resin to be used as the material of the substrate include polyacrylic acid ester, polymethacrylic acid ester, polycarbonate, polystyrene, polyvinyl acetate, and polyester. The resin is preferably polyacrylate or polymethacrylate. Among these, examples of the polymethacrylic acid ester include polyalkyl methacrylates (PAMAs) such as polymethyl methacrylate (PMMA), polyethyl methacrylate (PEMA), and polypropyl methacrylate. The polymethacrylate is preferably PMMA.

Known copolymers may also be used as the resin. Examples of the known copolymers include: acrylonitrile-styrene copolymers (AS resins), acrylonitrile-butadiene-styrene copolymers (ABS resins), and acrylonitrile/ethylene-propylene-diene/styrene copolymers (AES resins); and copolymers containing polymethacrylic acid ester such as methyl methacrylate-acrylonitrile-butadiene-styrene copolymers (MABS resins), methyl methacrylate-butadiene-styrene copolymers (MBS resins), and methyl methacrylate-styrene copolymers (MS resins).

The mode of immobilization of the polymer on the substrate surface may be either physical adsorption or covalent bonding. From the viewpoint of suppressing detachment or elution of the polymer from the substrate during washing of the substrate, the mode of immobilization is preferably covalent bonding.

Examples of the method of immobilizing the polymer on the substrate surface by physical adsorption include a method in which the polymer is dissolved in an organic solvent at a concentration of 0.05 to 10% by weight to prepare a polymer solution, and the solution is applied to the substrate surface by a known method such as immersion or spraying, followed by drying the substrate at room temperature or under warming. Examples of the organic solvent include ethanol, methanol, t-butyl alcohol, benzene, toluene, tetrahydrofuran, dioxane, dichloromethane, chloroform, acetone, and methyl ethyl ketone, which may be used as individual solvents or as a mixed solvent thereof. When the material of the substrate is a resin, a method using ethanol or methanol as the organic solvent is preferred since they do not deform the substrate, and can be easily dried.

Examples of the method of immobilizing the polymer to the substrate surface by covalent bonding include a method in which a functional group present in the polymer is reacted with a functional group present on the substrate surface, to allow formation of a covalent bond. Examples of the functional group present on the substrate surface include amino, carboxyl, hydroxy, and halogeno. The mode of the covalent bond may be any of an amide bond, ester bond, ether bond and the like. From the viewpoint of simplicity of bond formation and strength, amide bond is preferred.

The method employed to immobilize the polymer on the substrate surface by amide bond may be a method in which an amino group(s) present in the polymer is/are reacted with a carboxyl group(s) present on the substrate surface, or may be a method in which a carboxyl group(s) present in the polymer is/are reacted with an amino group(s) present on the substrate surface. It is more preferred to employ the method in which an amino group(s) present in the polymer is/are reacted with a carboxyl group(s) present on the substrate surface.

The polymer containing amino groups may be immobilized by condensation reaction with a carboxyl group(s) present on the substrate surface by directly reacting the amino group(s) in the polymer with the carboxyl group(s) present on the substrate surface using a condensing agent such as 1-(3-dimethylaminopropyl)-3-ethylcarbodiimide (another name: 1-ethyl-3-(3-dimethylaminopropyl)carbodiimide (EDC)) or 4-(4,6-dimethoxy-1,3,5-triazin-2-yl)-4-methylmorpholinium chloride (DMT-MM), or by first converting the carboxyl groups present on the substrate surface to an active ester using N-hydroxysuccinimide (NHS) or the like, followed by reaction with the amino groups in the polymer.

When no functional group reactive with the polymer is present on the substrate surface, a functional group reactive with the polymer may be produced on the substrate surface by a method appropriate for the material of the substrate.

Examples of the method of producing the functional group on a substrate surface made of a resin include a method in which the substrate is immersed in a solution that contains a compound containing the desired functional group, and a method in which the resin on the substrate surface is oxidized by exposure to UV, radiation, ozone, or plasma. Examples of the method of producing, as functional groups, carboxyl groups on a substrate surface made of a resin include a method in which the substrate surface is subjected to hydrolysis treatment with an alkali, acid or the like, a method in which the substrate surface is subjected to sonication in warm water, a method in which the substrate surface is irradiated with UV or ozone, and a method in which the substrate surface is exposed to oxygen plasma, argon plasma, or radiation. When the resin is a resin containing an ester structure in a side chain such as a polyacrylic acid ester or polymath-acrylic acid ester, the substrate may be immersed in an alkali or acid to hydrolyze the ester structure on the resin surface, to produce carboxyl groups on the substrate surface. More specifically, for example, a substrate made of a resin may be immersed in an aqueous solution of sodium hydroxide or sulfuric acid (at a concentration of preferably 1 N to 20 N), and left to stand at a temperature of preferably 30° C. to 80° C. for 1 hour to 100 hours. When the resin is a resin containing no ester structure in the side chains, carboxyl groups can be produced on the substrate surface by oxidizing carbon atoms on the resin surface by plasma treatment in the presence of oxygen.

Examples of the method of producing functional groups on a substrate surface made of glass include a method in which reaction with a silane coupling agent containing the desired functional group is performed. In another method that may be employed, a functional group introduced by reaction with a silane coupling agent is reacted with a compound containing another functional group, to convert the introduced functional group to the other functional group. Examples of the method of producing, as functional groups, carboxyl groups on a substrate surface made of glass include a method in which silanol groups on the substrate surface is reacted with a silane coupling agent such as 3-aminopropyltriethoxysilane to produce amino groups, and then the amino groups are reacted with a dicarboxylic anhydride such as succinic anhydride.

Examples of the method of producing functional groups on a substrate surface made of a metal include a method in which a silane coupling agent containing the desired functional group is reacted, and a method in which an alkanethiol containing the desired functional group is reacted. Examples of the method of producing, as functional groups, carboxyl groups on a substrate surface made of a metal include the above-described method of producing carboxyl groups on the substrate surface made of glass, and a method in which an alkanethiol containing a carboxyl group such as 5-carboxy-1-pentanethiol is reacted with the substrate.

As a method of producing functional groups on a substrate surface made of silicon wafer, the same method as the method of producing functional groups on the substrate surface made of glass may be employed.

The biochip comprises a selective-binding substance immobilized on a surface of a substrate through the above-described polymer. The "selective-binding substance" herein means a substance capable of directly or indirectly, selectively binding to a measurement target substance. Representative examples of the selective-binding substance include nucleic acids, proteins, saccharides, and other antigenic compounds. Examples of the nucleic acids include not only DNAs and RNAs, but also PNAs. A single-stranded nucleic acid having a particular base sequence can be a selective-binding substance since the nucleic acid selectively hybridizes with, and binds to, a single-stranded nucleic acid having a base sequence complementary to its base sequence or part thereof. Examples of the proteins include antibodies; antigen-binding fragments of antibodies such as Fab fragments and $F(ab')_2$ fragments; and various antigens. An antibody or an antigen-binding fragment thereof, or an antigen, can be a selective-binding substances since an antibody or an antigen-binding fragment thereof selectively binds to the corresponding antigen, and since an antigen selectively binds to the corresponding antibody. The saccharides are preferably polysaccharides, and examples of the saccharides include various antigens. An antigenic substance other than a protein or saccharide may also be immobilized. The selective-binding substance may be a commercially available substance, or may be obtained from a living cell or the like. The selective-binding substance is especially preferably a nucleic acid. Among nucleic acids, a nucleic acid having a length from 10 bases to 100 bases, which is called oligonucleic acid, is preferred since this nucleic acid can be artificially simply synthesized using a synthesizer, and since amino-group modification of an end of this nucleic acid can be simply carried out to allow simple immobilization of the nucleic acid on the substrate surface. From the viewpoint of stability of hybridization, the length of the nucleic acid is more preferably 20 to 100 bases. Preferred examples of the functional group with which the end of the nucleic acid may be modified include not only an amino group, but also a formyl group, an epoxy group, a carboxyl group, a hydroxy group, and a thiol group (sulfanyl group). Among these, an amino group is preferred. Methods of binding these functional groups to an end of nucleic acid are well known. For example, an amino group can be bound to an end of nucleic acid by binding an amidite reagent containing an amino group (see WO 2013/024694).

The selective-binding substance is immobilized on the substrate surface through a covalent bond(s) to the polymer bound to the substrate by the above method. The covalent bond(s) between the selective-binding substance and the polymer may be formed by direct binding to a reactive functional group in the polymer, or by binding using a known cross-linking agent. Examples of the known cross-linking agent include homolinkers such as 1,4-phenylene diisocyanate, 1,4-butanediol diglycidyl ether, and 1,4-phenylene diisothiocyanate; and heterolinkers such as 4-(N-maleimidomethyl)cyclohexanecarboxylic acid N-succinimidyl (SMCC) and maleimidoacetic acid N-succinimidyl (AMAS). More specifically, the covalent bonding between the selective-binding substance and the polymer can be achieved by, for example, immersing a substrate on which the polymer is immobilized, in a solution of 1,4-phenylene diisothiocyanate (at a concentration of preferably 10 to 50% by weight) in dimethyl sulfoxide, leaving the substrate to stand at a temperature of preferably 0° C. to 40° C. for 1 hour to 10 hours, bringing the substrate into contact with an aqueous solution of the selective-binding substance (at a concentration of preferably 0.1 to 10% by weight), and then leaving the substrate to stand at a temperature of preferably 0° C. to 40° C. for 1 hour to 100 hours.

The measurement target substance of the biochip is a substance to which the selective-binding substance selectively binds, and examples of the measurement target substance include nucleic acids, proteins and peptides. Examples of the nucleic acid include not only cell-free DNA, genomic DNA, messenger RNA, and microRNA, but also artificially synthesized nucleic acids. Examples of the protein include antibodies, antigens, cytokines, and allergens. The measurement target substance may be preliminarily labeled with a fluorescent substance or the like.

The measurement of the measurement target substance using the biochip may be carried out by a known method. The method usually includes: a step of bringing a specimen containing the measurement target substance into contact with a substrate surface, to allow formation of a complex with the selective-binding substance; and a step of detecting the complex formed. Usually, the substrate surface is washed before the detection step. The specimen is not limited as long as it contains the measurement target substance, or as long as it may potentially contain the measurement target substance. Specific examples of the specimen include: body fluids such as blood, plasma, and serum; and buffers containing the measurement target substance. The method of detecting the complex is not limited. The complex may be detected by a known method using fluorescence, chemiluminescence or the like. When the measurement target substance is labeled with a fluorescent substance or the like, it may be used for the detection of the complex, or the complex may be labeled with another fluorescent substance or the like followed by detecting the complex. When a signal value derived from the complex is measured from an area on which the selective-binding substance is immobilized, a noise value derived from the selective-binding substance that is non-specifically bound to the substrate may also be measured from an area on which the selective-binding substance is not immobilized, to use the noise value for judging the noise level.

EXAMPLES

Examples are shown below. However, this disclosure is not limited by the Examples.

Example 1

Biochips Using Partially Methoxycarbonylated Polyallylamine-Bound PMMA Substrates
(Substrates 2 to 6)

(1) Synthesis of Partially Methoxycarbonylated Polyallylamine (Formula (IV))

In a flask, 100 mL (263 mmol) of 15% by weight aqueous polyallylamine solution (number average molecular weight, 15,000; Nittobo Medical Co., Ltd., PAA-15C) was placed. While the temperature was kept at 50° C., 2.4 g of dimethyl carbonate (FUJIFILM Wako Pure Chemical Corporation, 26.3 mmol) was added dropwise to the aqueous solution for 15 minutes. After completion of the dropwise addition, the reaction was further allowed to proceed for 12 hours keeping the temperature at 50° C. Thereafter, the polymer solution was placed in a dialysis membrane (Por 3, manufactured by Spectra; molecular weight cutoff, 3500), and by-products were removed by dialysis operation in water. After purification, water was removed by freeze-drying, to obtain 10 mol % methoxycarbonylated polyallylamine. Measurement by $^1$H-NMR was carried out in heavy water and, from the ratio between the areas of the peak derived from methoxycarbonylated allylamine units (2.91 ppm) and the peak derived from unmodified allylamine units (2.45 ppm), the ratio of methoxycarbonylation (m/(m+n)) was confirmed to be 10 mol %.

By the same method, 30 mol % methoxycarbonylated polyallylamine was obtained using 7.1 g of dimethyl carbonate (manufactured by FUJIFILM Wako Pure Chemical Corporation, 78.9 mmol); 50 mol % methoxycarbonylated polyallylamine was obtained using 11.9 g of dimethyl carbonate (manufactured by FUJIFILM Wako Pure Chemical Corporation, 132 mmol); 70 mol % methoxycarbonylated polyallylamine was obtained using 16.6 g of dimethyl carbonate (manufactured by FUJIFILM Wako Pure Chemical Corporation, 184 mmol); and 90 mol % methoxycarbonylated polyallylamine was obtained using 21.3 g of dimethyl carbonate (manufactured by FUJIFILM Wako Pure Chemical Corporation, 237 mmol).

(IV)

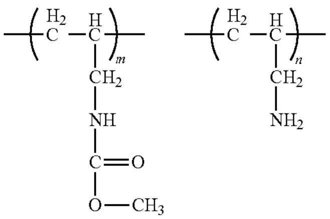

In Formula (IV), m and n each independently represent a positive number. Accordingly, m/(m+n) and n/(m+n) represent the molar ratios of those units.

(2) Preparation of NHS-Esterified PMMA Substrate (Substrate 1)

A plate made of polymethyl methacrylate (PMMA) (75 mm×25 mm×1 mm) was immersed in 10 N aqueous sodium hydroxide solution at 70° C. for 15 hours. Subsequently, the plate was washed with pure water, 0.1 N aqueous HCl solution, and pure water in this order. Thus, side chains of PMMA on the substrate surface were hydrolyzed to produce carboxyl groups.

Subsequently, 100 mg of N-hydroxysuccinimide (NHS) and 350 mg of 1-ethyl-3-(3-dimethylaminopropyl)carbodiimide (EDC) were dissolved in 400 mL of 2-morpholinoethanesulfonic acid monohydrate (MES) buffer (whose pH was adjusted to 5.0 with 0.1 N sodium hydroxide). To the resulting mixed solution, the above hydrolyzed PMMA substrate was immersed, and the solution was stirred for 1 hour using a microstirrer, to obtain an NHS-esterified PMMA substrate (Substrate 1).

(3) Preparation of Partially Methoxycarbonylated Polyallylamine-Bound PMMA Substrates
(Substrates 2 to 6)

The NHS-esterified PMMA substrate (Substrate 1) obtained in (2) was immersed in 400 mL of borate buffer in which the 10 mol % methoxycarbonylated polyallylamine obtained in (1) was dissolved at 1% by weight (100 mM, whose pH was adjusted to 10 with 1 N sodium hydroxide), and the buffer was stirred for 1 hour using a microstirrer. Thereafter, the substrate was immersed in 400 mL of a solution prepared by dissolving 100 mg of 1,4-phenylene diisothiocyanate as a cross-linking agent in dimethyl sulfoxide, and the solution was stirred for 1 hour using a microstirrer, to obtain a 10 mol % methoxycarbonylated polyallylamine-bound PMMA substrate (Substrate 2).

By the same method, a 30 mol % methoxycarbonylated polyallylamine-bound PMMA substrate (Substrate 3) was obtained using 30 mol % methoxycarbonylated polyallylamine; a 50 mol % methoxycarbonylated polyallylamine-bound PMMA substrate (Substrate 4) was obtained using 50 mol % methoxycarbonylated polyallylamine; a 70 mol % methoxycarbonylated polyall-ylamine-bound PMMA substrate (Substrate 5) was obtained using 70 mol % methoxycarbonylated polyallylamine; and a 90 mol % methoxycarbonylated polyallylamine-bound PMMA substrate (Substrate 6) was obtained using 90 mol % methoxycarbonylated polyallylamine.

(4) Immobilization of Probe DNA on Substrate

As a probe DNA, the following DNA having the base sequence of SEQ ID NO:1 was synthesized:

```
5'-AACTATACAACCTACTACCTCA-3'
(SEQ ID NO: 1: 23 bases, 5'-end aminated).
```

The DNA was dissolved in pure water at a concentration of 100 μM to provide a stock solution. The stock solution was 5-fold diluted with PBS (prepared by dissolving 8 g of NaCl, 2.9 g of $Na_2HPO_4.12H_2O$, 0.2 g of KCl, and 0.2 g of $K_2PO_4$ in pure water and then adding pure water to a final volume of 1 L; pH 7.4), to provide a spot solution. About 40 μL of the spot solution was taken, and used to provide 6×4=24 DNA spots in the center portion of each substrate prepared in (3) (Substrates 2 to 6), using a spotting robot (Nippon Laser & Electronics Lab. Co., Ltd.; GTMAS Stamp-2). Thereafter, each substrate was placed in a sealed plastic container, and incubated under conditions at 37° C. at a humidity of 100% for about 20 hours, to immobilize the probe DNA. Thereafter, the substrate was washed with pure water.

(5) Hybridization to Substrate on Which Probe DNA Is Immobilized

For total RNA derived from a prostate tissue (Thermo Fisher Scientific Inc.), miRNA was fluorescently labeled using a 3D-Gene (registered trademark) miRNA Labeling kit (Toray Industries, Inc.) according to a protocol designed by the manufacturer, to provide a stock solution. The stock solution was 50-fold diluted with a solution of 1% by weight BSA (bovine serum albumin), 5×SSC (wherein 5×SSC means a solution prepared by dissolving 43.8 g of NaCl and 22.1 g of trisodium citrate hydrate in pure water, and then adding pure water thereto to a final volume of 200 mL; a solution prepared by dissolving 43.8 g of NaCl and 22.1 g of trisodium citrate hydrate in pure water, and then adding pure water thereto to a final volume of 1 L, is referred to as 1×SSC; and its 10-fold concentrate and 5-fold dilution are referred to as 10×SSC and 0.2×SSC, respectively), 0.1% by weight SDS (sodium dodecyl sulfate), and 0.01% by weight salmon sperm DNA (wherein each concentration represents the final concentration), to provide a hybridization solution. To each of the substrates (Substrates 2 to 6) on which the probe DNA was immobilized, 100 μL of the hybridization solution was added dropwise, and a cover glass was placed thereon. The periphery of the cover glass was sealed with a paper bond to prevent drying of the hybridization solution. The resulting substrate was placed in a plastic container, and incubated under conditions at 35° C. at a humidity of 100% for 12 hours to perform hybridization. Thereafter, the cover glass was peeled off, and then the substrate was washed and dried.

(6) Fluorescence Measurement of Biochip after Hybridization

The substrate after the hybridization was placed in a "3D-Gene" (registered trademark) Scanner (Toray Industries, Inc.), and measurement was performed under the following conditions: excitation light, 635 nm; laser output, 100%; PMT 30. The results are shown in Table 1.

Example 2

Biochips Using Partially Acetylated Polyallylamine-Bound PMMA Substrates (Substrates 7 to 9)

(1) Synthesis of Partially Acetylated Polyallylamine (Formula (V))

In a flask, 100 mL (263 mmol) of 15% by weight aqueous polyallylamine solution (number average molecular weight, 15,000; Nittobo Medical Co., Ltd., PAA-15C) was placed. While the temperature was kept at 50° C., 8.1 g of acetic anhydride (FUJIFILM Wako Pure Chemical Corporation, 78.9 mmol) was added dropwise to the aqueous solution for 15 minutes. After completion of the dropwise addition, the reaction was further allowed to proceed for 12 hours keeping the temperature at 50° C. Thereafter, aqueous sodium hydroxide solution (FUJIFILM Wako Pure Chemical Corporation, 8 N) was added to the reaction solution until the pH became 11. The polymer solution was then placed in a dialysis membrane (Por 3, manufactured by Spectra; molecular weight cutoff, 3500), and by-products were removed by dialysis operation in water. After purification, water was removed by freeze-drying, to obtain 30 mol % acetylated polyallylamine. Measurement by $^1$H-NMR was carried out in heavy water and, from the ratio between the areas of the peak derived from acetylated allylamine units (2.87 ppm) and the peak derived from unmodified allylamine units (2.45 ppm), the ratio of acetylation (m/(m+n)) was confirmed to be 30 mol %.

By the same method, 50 mol % acetylated polyallylamine was obtained using 13.5 g (132 mmol) of acetic anhydride, and 70 mol % acetylated polyallylamine was obtained using 18.8 g (184 mmol) of acetic anhydride.

(V)

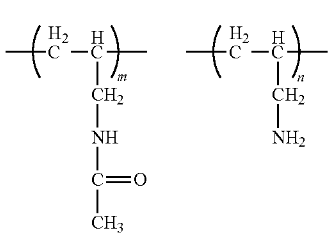

In Formula (V), m and n each independently represent a positive number. Accordingly, m/(m+n) and n/(m+n) represent the molar ratios of those units.

(2) Preparation of Partially Acetylated Polyallylamine-Bound PMMA Substrates (Substrates 7 to 9)

By the same methods as in (2) and (3) of Example 1, a 30 mol % acetylated polyallylamine-bound PMMA substrate (Substrate 7) was obtained using 30 mol % acetylated polyallylamine; a 50 mol % acetylated polyallylamine-bound PMMA substrate (Substrate 8) was obtained using 50 mol % acetylated polyallylamine; and a 70 mol % acetylated polyallylamine-bound PMMA substrate (Substrate 9) was obtained using 70 mol % acetylated polyallylamine.

(3) Immobilization of Probe DNA on Substrate, and Evaluation

The probe DNA was immobilized on each substrate obtained in (2), in the same manner as in (4) of Example 1 to obtain a biochip. In the same manner as in (5) and (6) of Example 1, the resulting biochip was subjected to hybridization, and then to fluorescence measurement. The results are shown in Table 1.

Example 3

Biochips Using Partially Carbamoylated Polyallylamine-Bound PMMA Substrates (Substrates 10 to 12)

(1) Synthesis of Partially Carbamoylated Polyallylamine (Formula (VI))

In a flask, 100 mL (263 mol) of 15% by weight aqueous polyallylamine solution (number average molecular weight, 15,000; Nittobo Medical Co., Ltd., PAA-15C) was placed, and 21.9 g (263 mol) of concentrated hydrochloric acid (manufactured by FUJIFILM Wako Pure Chemical Corporation) was added dropwise thereto under ice-cooling. Subsequently, the resulting mixture was warmed to 50° C., and 68.4 g of 7.5% by weight aqueous sodium cyanate solution (manufactured by FUJIFILM Wako Pure Chemical Corporation; 78.9 mmol) was added dropwise thereto, followed by allowing the reaction to proceed for 24 hours. Thereafter, aqueous sodium hydroxide solution (FUJIFILM Wako Pure Chemical Corporation, 8 N) was added to the reaction solution until the pH became 11. The polymer solution was then placed in a dialysis membrane (Por 3, manufactured by Spectra; molecular weight cutoff, 3500), and by-products were removed by dialysis operation in water. After purification, water was removed by freeze-drying, to obtain 30 mol % carbamoylated polyallylamine. Measurement by $^1$H-NMR was carried out in heavy water, and, from the ratio between the areas of the peak derived from carbamoylated allylamine units (2.88 ppm) and the peak derived from unmodified allylamine units (2.51 ppm), the ratio of carbamoylation (m/(m+n)) was confirmed to be 30 mol %.

By the same method, 50 mol % carbamoylated polyallylamine was obtained using 114.4 g (132 mmol) of 7.5% by weight aqueous sodium cyanate solution, and 70 mol % carbamoylated polyallylamine was obtained using 159.5 g (184 mmol) of 7.5% by weight aqueous sodium cyanate solution.

(VI)

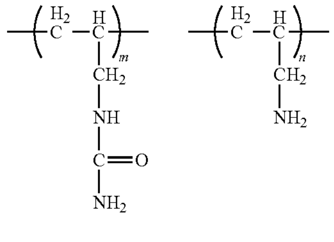

In Formula (VI), m and n each independently represent a positive number. Accordingly, m/(m+n) and n/(m+n) represent the molar ratios of those units.

(2) Preparation of Partially Carbamoylated Polyallylamine-Bound PMMA Substrates (Substrates 10 to 12)

By the same methods as in (2) and (3) of Example 1, a 30 mol % carbamoylated polyallylamine-bound PMMA substrate (Substrate 10) was obtained using 30 mol % carbamoylated polyallylamine; a 50 mol % carbamoylated polyallylamine-bound PMMA substrate (Substrate 11) was obtained using 50 mol % carbamoylated polyallylamine; and a 70 mol % carbamoylated polyallylamine-bound PMMA substrate (Substrate 12) was obtained using 70 mol % carbamoylated polyallylamine.

(3) Immobilization of Probe DNA on Substrate, and Evaluation

The probe DNA was immobilized on each substrate obtained in (2), in the same manner as in (4) of Example 1 to obtain a biochip. In the same manner as in (5) and (6) of Example 1, the resulting biochip was subjected to hybridization, and then to fluorescence measurement. The results are shown in Table 1.

Comparative Example 1

Biochip Using NHS-Esterified PMMA Substrate (Substrate 1)

The probe DNA was immobilized on the NHS-esterified PMMA substrate (Substrate 1) obtained in (2) of Example 1, in the same manner as in (4) of Example 1 to obtain a biochip. In the same manner as in (5) and (6) of Example 1, the resulting biochip was subjected to hybridization, and then fluorescence measurement. The results are shown in Table 1.

Comparative Example 2

Polyethyleneimine-Bound PMMA Substrate (Substrate 13)

(1) Preparation of Polyethyleneimine-Bound PMMA Substrate (Substrate 13)

By the same methods as in (2) and (3) of Example 1, a polyethyleneimine-bound PMMA substrate (Substrate 13) was obtained using polyethyleneimine (number average molecular weight, 10,000; Nippon Shokubai Co., Ltd., SP-200).

(2) Immobilization of Probe DNA on Substrate, and Evaluation

The probe DNA was immobilized on the substrate obtained in (1), in the same manner as in (4) of Example 1 to obtain a biochip. In the same manner as in (5) and (6) of Example 1, the resulting biochip was subjected to hybridization, and then fluorescence measurement. The results are shown in Table 1.

Comparative Example 3

Biochip Using Polyallylamine-Bound PMMA Substrate (Substrate 14)

(1) Preparation of Polyallylamine-Bound PMMA Substrate (Substrates 14)

By the same methods as in (2) and (3) of Example 1, a polyallylamine-bound PMMA substrate (Substrate 14) was obtained using polyallylamine (number average molecular weight, 15,000; Nittobo Medical Co., Ltd., PAA-15C).

(2) Immobilization of Probe DNA on Substrate, and Evaluation

The probe DNA was immobilized on the substrate obtained in (1), in the same manner as in (4) of Example 1 to obtain a biochip. In the same manner as in (5) and (6) of Example 1, the resulting biochip was subjected to hybridization, and then fluorescence measurement. The results are shown in Table 1.

Comparative Example 4

Biochip Using Partially Carboxymethylated Polyallylamine-Bound PMMA Substrate (Substrate 15)

(1) Synthesis of Partially Carboxymethylated Polyallylamine (Formula (VII))

In a flask, 100 mL (263 mol) of 15% by weight aqueous polyallylamine solution (number average molecular weight, 15,000; Nittobo Medical Co., Ltd., PAA-15C) was placed, and the solution was warmed to 50° C., followed by adding 9.1 g of bromoacetic acid (manufactured by FUJIFILM Wako Pure Chemical Corporation, 65.8 mmol) dropwise thereto and allowing the reaction to proceed for 24 hours. Thereafter, aqueous sodium hydroxide solution (FUJIFILM Wako Pure Chemical Corporation, 8 N) was added to the reaction solution until the pH became 11. The polymer solution was then placed in a dialysis membrane (Por 3, manufactured by Spectra; molecular weight cutoff, 3500), and by-products were removed by dialysis operation in water. After purification, water was removed by freeze-drying, to obtain 25 mol % carboxymethylated polyallylamine. Measurement by $^{1}$H-NMR was carried out in heavy water and, from the ratio between the areas of the peak derived from carboxymethylated allylamine units (2.61 ppm) and the peak derived from unmodified allylamine units (2.51 ppm), the ratio of carboxymethylation (m/(m+n)) was confirmed to be 25 mol %.

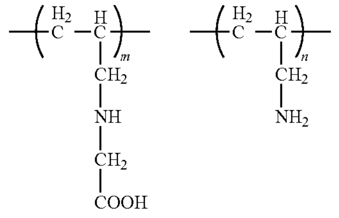

(VII)

In Formula (VII), m and n each independently represent a positive number. Accordingly, m/(m+n) and n/(m+n) represent the molar ratios of those units.

(2) Preparation of Partially Carboxymethylated Polyallylamine-Bound PMMA Substrate (Substrate 15)

By the same methods as in (2) and (3) of Example 1, a 25 mol % carboxymethylated polyallylamine-bound PMMA substrate (Substrate 15) was obtained using 25 mol % carboxymethylated polyallylamine.

(3) Immobilization of Probe DNA on Substrate, and Evaluation

The probe DNA was immobilized on the substrate obtained in (2), in the same manner as in (4) of Example 1 to obtain a biochip. In the same manner as in (5) and (6) of Example 1, the resulting biochip was subjected to hybridization, and then to fluorescence measurement. The results are shown in Table 1.

TABLE 1

| | Substrate | Polymer type | Unit ratio (m/(m + n)) | Signal value | Noise value | SN ratio |
|---|---|---|---|---|---|---|
| Example 1 | Substrate 2 | Partially methoxycarbonylated | 10 mol % | 1445 | 105 | 13.7 |
| | Substrate 3 | polyallylamine | 30 mol % | 1558 | 102 | 15.2 |
| | Substrate 4 | | 50 mol % | 1866 | 84 | 22.2 |
| | Substrate 5 | | 70 mol % | 1747 | 83 | 21.0 |
| | Substrate 6 | | 90 mol % | 1115 | 75 | 14.8 |
| Example 2 | Substrate 7 | Partially acetylated | 30 mol % | 1165 | 87 | 13.3 |
| | Substrate 8 | polyallylamine | 50 mol % | 1364 | 77 | 17.7 |
| | Substrate 9 | | 70 mol % | 1385 | 76 | 18.2 |
| Example 3 | Substrate 10 | Partially carbamoylated | 30 mol % | 1095 | 90 | 12.1 |
| | Substrate 11 | polyallylamine | 50 mol % | 1218 | 87 | 14.0 |
| | Substrate 12 | | 70 mol % | 1267 | 80 | 15.8 |
| Comparative Example 1 | Substrate 1 | None | — | 522 | 66 | 7.9 |
| Comparative Example 2 | Substrate 13 | Polyethyleneimine | — | 752 | 98 | 7.7 |
| Comparative Example 3 | Substrate 14 | Polyallylamine | — | 1044 | 125 | 8.3 |
| Comparative Example 4 | Substrate 15 | Partially carboxymethylated polyallylamine | 25 mol % | 945 | 95 | 9.9 |

Table 1 shows the fluorescence value (signal value) of the part on which the probe DNA was immobilized, the fluorescence value (noise value) of the part on which the probe DNA was not immobilized, and the ratio of the signal value to the noise value (SN ratio), in the substrate after the hybridization. The fluorescence detected herein is derived from the fluorescent dye contained in the labeling kit, and RNA fluorescently labeled by the labeling kit. The larger their binding amounts, the higher the value. The signal value corresponds to the amount of fluorescently labeled RNA bound to the probe DNA by the hybridization, which RNA has a sequence complementary to the probe DNA. On the other hand, the noise value corresponds to the amount of fluorescent dye and fluorescently labeled RNA that are non-specifically bound to the substrate. The value of the SN ratio increases as the amount of RNA bound to the probe DNA by the hybridization increases, and as the amount of RNA and fluorescent dye non-specifically bound to the substrate decreases. The SN ratio was therefore used as an index of the detection sensitivity of the biochip.

The substrates on which partially methoxycarbonylated polyallylamine obtained by modification of side-chain amino groups of polyallylamine was bound (Example 1, Substrates 2 to 6) showed higher SN ratios compared to the substrate on which no polymer was bound (Comparative Example 1, Substrate 1), and even compared to the substrate on which polyethyleneimine was bound (Comparative Example 2, Substrate 13) and the substrate on which polyallylamine was bound (Comparative Example 3, Substrate 14). This is assumed to be due to the effect of suppression of non-specific adsorption of the fluorescent dye, which causes an increase in the noise value, by the modification with the methoxycarbonyl group; and due to improvement of the efficiency of hybridization by the control of the density of reactive functional groups on the substrate surface.

We also found the same effect for the substrates on which partially acetylated polyallylamine was bound (Example 2, Substrates 7 to 9) and the substrates on which partially carbamoylated polyallylamine was bound (Example 3, Substrates 10 to 12). On the other hand, the effect was not found for the substrate on which partially carboxymethylated polyallylamine was bound (Comparative Example 4, Substrate 15). From these results, we found that the type of the functional group for the modification of the polymer is important to obtain a biochip excellent in both the signal value and the SN ratio.

Example 4

Biochips Using Partially Propanamide-Modified Polyallylamine-Bound PMMA Substrates (Substrates 16 to 18)

(1) Synthesis of Partially Propanamide-Modified Polyallylamine (Formula (VIII))

In a flask, 100 mL (263 mmol) of 15% by weight aqueous polyallylamine solution (number average molecular weight, 15,000; Nittobo Medical Co., Ltd., PAA-15C) was placed. While the temperature was kept at 50° C., an aqueous solution prepared by dissolving 5.6 g of acrylamide (manufactured by FUJIFILM Wako Pure Chemical Corporation, 78.9 mmol) in 50 mL of distilled water was added dropwise to the above aqueous solution for 15 minutes. After completion of the dropwise addition, the reaction was further allowed to proceed for 12 hours keeping the temperature at 50° C. Thereafter, the polymer solution was placed in a dialysis membrane (Por 3, manufactured by Spectra; molecular weight cutoff, 3500), and by-products were removed by dialysis operation in water. After purification, water was removed by freeze-drying to obtain 30 mol % propanamide-modified polyallylamine. Measurement by $^1$H-NMR was carried out in heavy water and, from the ratio between the areas of the peak derived from propanamide-modified allylamine units (2.62 ppm) and the peak derived from unmodified allylamine units (2.45 ppm), the ratio of propanamide modification (m/(m+n)) was confirmed to be 30 mol %.

By the same method, 50 mol % propanamide-modified polyallylamine was obtained using 9.4 g of acrylamide (manufactured by FUJIFILM Wako Pure Chemical Corporation, 132 mmol), and 70 mol % propanamide-modified polyallylamine was obtained using 13.1 g of acrylamide (manufactured by FUJIFILM Wako Pure Chemical Corporation, 184 mmol).

(VIII)

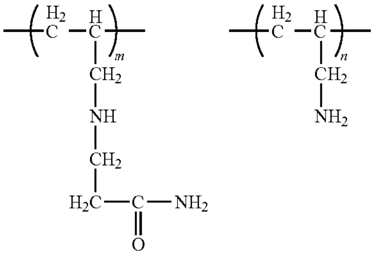

In Formula (VIII), m and n each independently represent a positive number. Accordingly, m/(m+n) and n/(m+n) represent the molar ratios of those units.

(2) Preparation of NHS-Esterified PMMA Substrate (Substrate 1)

By the same method as in (2) of Example 1, an NHS-esterified PMMA Substrate (Substrate 1) was prepared.

(3) Preparation of Partially Propanamide-Modified Polyallylamine-Bound PMMA Substrates (Substrates 16 to 18)

The NHS-esterified PMMA substrate (Substrate 1) prepared in (2) was immersed in 400 mL of borate buffer in which the 30 mol % propanamide-modified polyallylamine obtained in (1) was dissolved at 1% by weight (100 mM, whose pH was adjusted to 10 with 1 N sodium hydroxide), and the buffer was stirred for 1 hour using a microstirrer. Thereafter, the substrate was immersed in 400 mL of a solution prepared by dissolving 100 mg of 1,4-phenylene diisothiocyanate as a cross-linking agent in dimethyl sulfoxide, and the solution was stirred for 1 hour using a microstirrer to obtain a 30 mol % propanamide-modified polyallylamine-bound PMMA substrate (Substrate 16).

By the same method, a 50 mol % propanamide-modified polyallylamine-bound PMMA substrate (Substrate 17) was obtained using 50 mol % propanamide-modified polyallylamine; and a 70 mol % propanamide-modified polyallylamine-bound PMMA substrate (Substrate 18) was obtained using 70 mol % propanamide-modified polyallylamine.

(4) Immobilization of Probe DNA on Substrate

Similarly to (4) of Example 1, DNA having the base sequence of SEQ ID NO:1 (23 bases, 5'-end aminated) was used as the probe DNA. By the same method as in Example 1, the probe DNA was immobilized on each substrate.

(5) Hybridization to Substrate on Which Probe DNA Is Immobilized

By the same method as in (5) of Example 1, hybridization to the substrate on which the probe DNA was immobilized was carried out.

(6) Fluorescence Measurement of Biochip after Hybridization

By the same method as in (6) of Example 1, the biochip after the hybridization was subjected to fluorescence measurement. The results are shown in Table 2.

Example 5

Biochip Using Partially N,N-Dimethylpropanamide-Modified Polyallylamine-Bound PMMA Substrate (Substrate 19)

(1) Synthesis of Partially N,N-Dimethylpropanamide-Modified Polyallylamine (Formula (IX))

In a flask, 100 mL (263 mmol) of 15% by weight aqueous polyallylamine solution (number average molecular weight, 15,000; Nittobo Medical Co., Ltd., PAA-15C) was placed. While the temperature was kept at 50° C., an aqueous solution prepared by dissolving 13.1 g of N,N-dimethylacrylamide (FUJIFILM Wako Pure Chemical Corporation, 132 mmol) in 50 mL of distilled water was added dropwise to the above aqueous solution for 15 minutes. After completion of the dropwise addition, the reaction was further allowed to proceed for 12 hours keeping the temperature at 50° C. Thereafter, the polymer solution was placed in a dialysis membrane (Por 3, manufactured by Spectra; molecular weight cutoff, 3500), and by-products were removed by dialysis operation in water. After purification, water was removed by freeze-drying, to obtain 50 mol % N,N-dimethylpropanamide-modified polyallylamine. Measurement by 1H-NMR was carried out in heavy water and, from the ratio between the areas of the peak derived from N,N-dimethylpropanamide-modified allylamine units (2.62 ppm) and the peak derived from unmodified allylamine units (2.45 ppm), the ratio of N,N-dimethylpropanamide modification (m/(m+n)) was confirmed to be 50 mol %.

(IX)

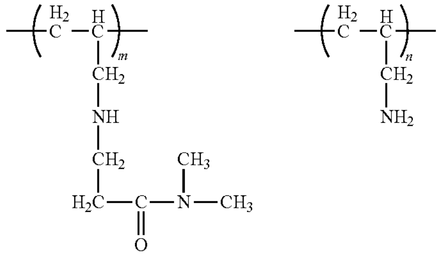

In Formula (IX), m and n each independently represent a positive number. Accordingly, m/(m+n) and n/(m+n) represent the molar ratios of those units.

(2) Preparation of Partially N,N-Dimethylpropanamide-Modified Polyallylamine-Bound PMMA Substrate (Substrate 19)

By the same methods as in (2) and (3) of Example 4, a 50 mol % N,N-dimethylpropanamide-modified polyallylamine-bound PMMA substrate (Substrate 19) was obtained using 50 mol % N,N-dimethylpropanamide-modified polyallylamine.

(3) Immobilization of Probe DNA on Substrate, and Evaluation

The probe DNA was immobilized on each substrate obtained in (2), in the same manner as in (4) of Example 4 to obtain a biochip. In the same manner as in (5) and (6) of Example 4, the resulting biochip was subjected to hybridization, and then to fluorescence measurement. The results are shown in Table 2.

Example 6

Biochip Using Partially N,N-Diethylpropanamide-Modified Polyallylamine-Bound PMMA Substrate (Substrate 20)

(1) Synthesis of Partially N,N-Diethylpropanamide-Modified Polyallylamine (Formula (X))

In a flask, 100 mL (263 mmol) of 15% by weight aqueous polyallylamine solution (number average molecular weight, 15,000; Nittobo Medical Co., Ltd., PAA-15C) was placed. While the temperature was kept at 50° C., an aqueous solution prepared by dissolving 16.8 g of N,N-diethylacrylamide (FUJIFILM Wako Pure Chemical Corporation, 132 mmol) in 50 mL of distilled water was added dropwise to the above aqueous solution for 15 minutes. After completion of the dropwise addition, the reaction was further allowed to proceed for 12 hours keeping the temperature at 50° C. Thereafter, the polymer solution was placed in a dialysis membrane (Por 3, manufactured by Spectra; molecular weight cutoff, 3500), and by-products were removed by dialysis operation in water. After purification, water was removed by freeze-drying, to obtain 50 mol % N,N-diethylpropanamide-modified polyallylamine. Measurement by $^1$H-NMR was carried out in heavy water and, from the ratio between the areas of the peak derived from N,N-diethylpropanamide-modified allylamine units (2.64 ppm) and the peak derived from unmodified allylamine units (2.45 ppm), the ratio of N,N-diethylpropanamide modification (m/(m+n)) was confirmed to be 50 mol %.

(X)

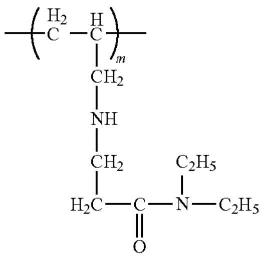

In Formula (X), m and n each independently represent a positive number. Accordingly, m/(m+n) and n/(m+n) represent the molar ratios of those units.

(2) Preparation of Partially N,N-Diethylpropanamide-Modified Polyallylamine-Bound PMMA Substrate (Substrate 20)

By the same methods as in (2) and (3) of Example 4, a 50 mol % N,N-diethylpropanamide-modified polyallylamine-bound PMMA substrate (Substrate 20) was obtained using 50 mol % N,N-diethylpropanamide-modified polyallylamine.

(3) Immobilization of Probe DNA on Substrate, and Evaluation

The probe DNA was immobilized on each substrate obtained in (2), in the same manner as in (4) of Example 4 to obtain a biochip. In the same manner as in (5) and (6) of Example 4, the resulting biochip was subjected to hybridization, and then to fluorescence measurement. The results are shown in Table 2.

Example 7

Biochip Using Partially N-Isopropylpropanamide-Modified Polyallylamine-Bound PMMA Substrate (Substrate 21)

(1) Synthesis of Partially N-Isopropylpropanamide-Modified Polyallylamine (Formula (XI))

In a flask, 100 mL (263 mmol) of 15% by weight aqueous polyallylamine solution (number average molecular weight, 15,000; Nittobo Medical Co., Ltd., PAA-15C) was placed. While the temperature was kept at 50° C., an aqueous solution prepared by dissolving 14.9 g of N-isopropylacrylamide (FUJIFILM Wako Pure Chemical Corporation, 132 mmol) in 50 mL of distilled water was added dropwise to the above aqueous solution for 15 minutes. After completion of the dropwise addition, the reaction was further allowed to proceed for 12 hours keeping the temperature at 50° C. Thereafter, the polymer solution was placed in a dialysis membrane (Por 3, manufactured by Spectra; molecular weight cutoff, 3500), and by-products were removed by dialysis operation in water. After purification, water was removed by freeze-drying, to obtain 50 mol % N-isopropylpropanamide-modified polyallylamine. Measurement by $^1$H-NMR was carried out in heavy water and, from the ratio between the areas of the peak derived from N-isopropylpropanamide-modified allylamine units (2.60 ppm) and the peak derived from unmodified allylamine units (2.45 ppm), the ratio of N-isopropylpropanamide modification (m/(m+n)) was confirmed to be 50 mol %.

(XI)

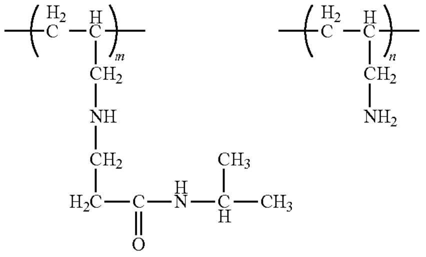

In Formula (XI), m and n each independently represent a positive number. Accordingly, m/(m+n) and n/(m+n) represent the molar ratios of those units.

(2) Preparation of Partially N-Isopropylpropanamide-Modified Polyallylamine-Bound PMMA Substrate (Substrate 7)

By the same methods as in (2) and (3) of Example 4, a 50 mol % N-isopropylpropanamide-modified polyallylamine-bound PMMA substrate (Substrate 21) was obtained using 50 mol % N-isopropylpropanamide-modified polyallylamine.

(3) Immobilization of Probe DNA on Substrate, and Evaluation

The probe DNA was immobilized on each substrate obtained in (2), in the same manner as in (4) of Example 4 to obtain a biochip. In the same manner as in (5) and (6) of Example 4, the resulting biochip was subjected to hybridization, and then to fluorescence measurement. The results are shown in Table 2. For simplifying comparison, Table 2 also shows the results of Comparative Examples 1 to 4 shown in Table 1.

TABLE 2

| | Substrate | Polymer type | Unit ratio (m/(m + n)) | Signal value | Noise value | SN ratio |
|---|---|---|---|---|---|---|
| Example 4 | Substrate 16 | Partially propanamide-modified polyallylamine | 30 mol % | 1276 | 88 | 14.5 |
| | Substrate 17 | | 50 mol % | 1492 | 82 | 18.2 |
| | Substrate 18 | | 70 mol % | 1480 | 80 | 18.5 |
| Example 5 | Substrate 19 | Partially N,N-dimethylpropanamide-modified polyallylamine | 50 mol % | 1215 | 90 | 13.5 |
| Example 6 | Substrate 20 | Partially N,N-diethylpropanamide-modified polyallylamine | 50 mol % | 1203 | 94 | 12.8 |

TABLE 2-continued

| | Substrate | Polymer type | Unit ratio (m/(m + n)) | Signal value | Noise value | SN ratio |
|---|---|---|---|---|---|---|
| Example 7 | Substrate 21 | PartiallyN-isopropylpropanamide-modified polyallylamine | 50 mol % | 1122 | 92 | 12.2 |
| Comparative Example 1 | Substrate 1 | None | — | 522 | 66 | 7.9 |
| Comparative Example 2 | Substrate 13 | Polyethyleneimine | — | 752 | 98 | 7.7 |
| Comparative Example 3 | Substrate 14 | Polyallylamine | — | 1044 | 125 | 8.3 |
| Comparative Example 4 | Substrate 15 | Partially carboxymethylated polyallylamine | 25 mol % | 945 | 95 | 9.9 |

Example 8

Biochips Comprising Albumen Allergen Immobilized on Partially Methoxycarbonyl-Modified Polyallylamine-Bound PMMA Substrates (Substrates 3 to 5)

(1) Immobilization of Albumen Allergen on Substrates

A lyophilized powder of albumen allergen was obtained from GREER, and the lyophilized powder was dissolved in pure water to a protein concentration of 1.0 mg/mL, to provide a spot solution. Using a spotting robot (Nippon Laser & Electronics Lab. Co., Ltd.; GTMAS Stamp-2), 6×4=24 albumen allergen spots were provided in the center portion of each substrate prepared in (3) of Example 1 (Substrates 3 to 5). Thereafter, each substrate was placed in a sealed plastic container, and incubated under conditions at 37° C. at a humidity of 100% for about 20 hours, to immobilize the albumen allergen. Thereafter, the substrate was washed with phosphate buffered saline (0.05% Tween 20 (trade name)).

(2) Contacting of Albumen Allergy-Positive Human Serum with Substrate on Which Albumen Allergen Is Immobilized An albumen allergy-positive human serum obtained from PlasmaLab was diluted 3-fold with phosphate buffered saline, and 50 μL of the resulting dilution was added dropwise to the substrate prepared in (1), followed by sealing the substrate by placing a gap cover glass (manufactured by Matsunami Glass Ind., Ltd.; 24 mm×25 mm; gap size, 20 μm) thereon. After allowing the reaction to proceed at 37° C. for 2 hours, the gap cover glass was removed, and the substrate was washed with phosphate buffered saline (0.05% Tween 20 (trade name)).

(3) Detection of Albumen Allergen-Specific IgE Antibody

A 1.0 mg/mL solution of Dylight-650 dye-labeled anti-human IgE goat polyclonal antibody (manufactured by Novus biologicals) was diluted 1000-fold with phosphate buffered saline (0.05% Tween 20 (trade name)) supplemented with 1% by weight bovine serum albumin. To the substrate brought into contact with human serum in (2), 50 μL of this dilution was added dropwise. A gap cover glass was then placed thereon, and the reaction was allowed to proceed at room temperature for 1 hour. Thereafter, the gap cover glass was removed, and the substrate was washed with phosphate buffered saline (0.05% Tween 20 (trade name)).

The substrate was then placed in a "3D-Gene" (registered trademark) Scanner (Toray Industries, Inc.), and measurement was performed under the following conditions: excitation light, 635 nm; laser output, 100%; PMT 30. The results are shown in Table 3.

Example 9

Biochips Comprising Albumen Allergen Immobilized on Partially Ethoxycarbonyl-Modified Polyallylamine-Bound PMMA Substrates (Substrates 22 to 24)

(1) Synthesis of Partially Ethoxycarbonyl-Modified Polyallylamine (Chemical Formula (XII))

In a flask, 100 mL (263 mmol) of 15% by weight aqueous polyallylamine solution (number average molecular weight, 15,000; Nittobo Medical Co., Ltd., PAA-15C) was placed. While the temperature was kept at 50° C., 9.32 g of diethyl carbonate (manufactured by FUJIFILM Wako Pure Chemical Corporation, 78.9 mmol) was added dropwise to the aqueous solution for 15 minutes. After completion of the dropwise addition, the reaction was further allowed to proceed for 12 hours keeping the temperature at 50° C. Thereafter, the polymer solution was placed in a dialysis membrane (Por 3, manufactured by Spectra; molecular weight cutoff, 3500), and by-products were removed by dialysis operation in water. After purification, water was removed by freeze-drying, to obtain 30 mol % ethoxycarbonylated polyallylamine. Measurement by 1H-NMR was carried out in heavy water and, from the ratio between the areas of the peak derived from ethoxycarbonylated allylamine units (2.87 ppm) and the peak derived from unmodified allylamine units (2.47 ppm), the ratio of ethoxycarbonyl modification (m/(m+n)) was confirmed to be 30 mol %.

By the same method, 50 mol % ethoxycarbonyl-modified polyallylamine was obtained using 15.6 g of diethyl carbonate (manufactured by FUJIFILM Wako Pure Chemical Corporation, 132 mmol), and 70 mol % ethoxycarbonyl-modified polyallylamine was obtained using 21.8 g of diethyl carbonate (manufactured by FUJIFILM Wako Pure Chemical Corporation, 184 mmol).

(XII)

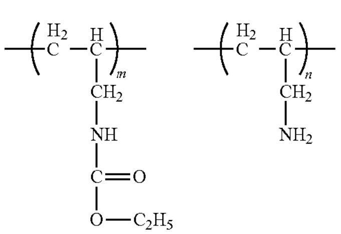

(2) Preparation of Partially Ethoxycarbonyl-Modified Polyallylamine-Bound PMMA Substrates (Substrates 22 to 24)

By the same methods as in (2) and (3) of Example 1, a 30 mol % ethoxycarbonyl-modified polyallylamine-bound PMMA substrate (Substrate 22) was obtained using 30 mol % ethoxycarbonyl-modified polyallylamine; a 50 mol % ethoxycarbonyl-modified polyallylamine-bound PMMA substrate (Substrate 23) was obtained using 50 mol % ethoxycarbonyl-modified polyallylamine; and a 70 mol % ethoxycarbonyl-modified polyallylamine-bound PMMA substrate (Substrate 24) was obtained using 70 mol % ethoxycarbonyl-modified polyallylamine.

(3) Immobilization of Albumen Allergen on Substrate, and Evaluation

Albumen allergen was immobilized on each substrate obtained in (2), in the same manner as in (1) of Example 8 to obtain a biochip. In the same manner as in (2) and (3) of Example 8, the resulting biochip was subjected to fluorescence measurement after contact with the albumen allergy-positive human serum. The results are shown in Table 3.

Example 10

Biochips Comprising Albumen Allergen Immobilized on Partially Propyloxycarbonyl-Modified Polyallylamine-Bound PMMA Substrates (Substrates 25 to 27)

(1) Synthesis of Partially Propyloxycarbonyl-Modified Polyallylamine (Chemical Formula (XIII))

In a flask, 100 mL (263 mmol) of 15% by weight aqueous polyallylamine solution (number average molecular weight, 15,000; Nittobo Medical Co., Ltd., PAA-15C) was placed. While the temperature was kept at 50° C., 11.5 g of dipropyl carbonate (manufactured by Sigma-Aldrich, 78.9 mmol) was added dropwise to the aqueous solution for 15 minutes. After completion of the dropwise addition, the reaction was further allowed to proceed for 12 hours keeping the temperature at 50° C. Thereafter, the polymer solution was placed in a dialysis membrane (Por 3, manufactured by Spectra; molecular weight cutoff, 3500), and by-products were removed by dialysis operation in water. After purification, water was removed by freeze-drying, to obtain 30 mol % propyloxycarbonylated polyallylamine. Measurement by 1H-NMR was carried out in heavy water and, from the ratio between the areas of the peak derived from propyloxycarbonylated allylamine units (2.85 ppm) and the peak derived from unmodified allylamine units (2.50 ppm), the ratio of propyloxycarbonyl modification (m/(m+n)) was confirmed to be 30 mol %.

By the same method, 50 mol % propyloxycarbonyl-modified polyallylamine was obtained using 19.3 g of dipropyl carbonate (manufactured by Sigma-Aldrich, 132 mmol), and 70 mol % propyloxycarbonyl-modified polyallylamine was obtained using 26.9 g of dipropyl carbonate (manufactured by Sigma-Aldrich, 184 mmol).

(XIII)

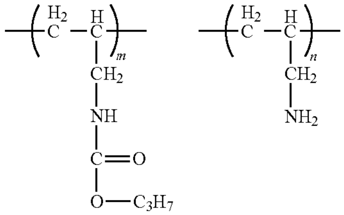

(2) Preparation of Partially Propyloxycarbonyl-Modified Polyallylamine-Bound PMMA Substrates (Substrates 25 to 27)

By the same methods as in (2) and (3) of Example 1, a 30 mol % propyloxycarbonyl-modified polyallylamine-bound PMMA substrate (Substrate 25) was obtained using 30 mol % propyloxycarbonyl-modified polyallylamine; a 50 mol % propyloxycarbonyl-modified polyallylamine-bound PMMA substrate (Substrate 26) was obtained using 50 mol % propyloxycarbonyl-modified polyallylamine; and a 70 mol % propyloxycarbonyl-modified polyallylamine-bound PMMA substrate (Substrate 27) was obtained using 70 mol % propyloxycarbonyl-modified polyallylamine.

(3) Immobilization of Albumen Allergen on Substrate, and Evaluation

Albumen allergen was immobilized on each substrate obtained in (2), in the same manner as in (1) of Example 8 to obtain a biochip. In the same manner as in (2) and (3) of Example 8, the resulting biochip was subjected to fluorescence measurement after contact with the albumen allergy-positive human serum. The results are shown in Table 3.

Example 11

Biochip Comprising Albumen Allergen Immobilized on Partially Propanamide-Modified Polyallylamine-Bound PMMA Substrate (Substrate 17)

(1) Immobilization of Albumen Allergen on Substrate, and Evaluation

Albumen allergen was immobilized on the Substrate 17 obtained in (3) of Example 4, in the same manner as in (1) of Example 8 to obtain a biochip. In the same manner as in (2) and (3) of Example 8, the resulting biochip was subjected to fluorescence measurement after contact with the albumen allergy-positive human serum. The results are shown in Table 3.

Example 12

Biochip Comprising Albumen Allergen Immobilized on Partially N,N-Dimethylpropanamide-Modified Polyallylamine-Bound PMMA Substrate (Substrate 19)

(1) Immobilization of Albumen Allergen on Substrate, and Evaluation

Albumen allergen was immobilized on the Substrate 19 obtained in (3) of Example 5, in the same manner as in (1) of Example 8 to obtain a biochip. In the same manner as in (2) and (3) of Example 8, the resulting biochip was subjected to fluorescence measurement after contact with the albumen allergy-positive human serum. The results are shown in Table 3.

Example 13

Biochip Comprising Albumen Allergen Immobilized on Partially N,N-Diethylpropanamide-Modified Polyallylamine-Bound PMMA Substrate (Substrate 20)

(1) Immobilization of Albumen Allergen on Substrate, and Evaluation

Albumen allergen was immobilized on the Substrate 20 obtained in (3) of Example 6, in the same manner as in (1) of Example 8 to obtain a biochip. In the same manner as in (2) and (3) of Example 8, the resulting biochip was subjected to fluorescence measurement after contact with the albumen allergy-positive human serum. The results are shown in Table 3.

Example 14

Biochip Comprising Albumen Allergen Immobilized on Partially N-Isopropylpropanamide-Modified Polyallylamine-Bound PMMA Substrate (Substrate 21)

(1) Immobilization of Albumen Allergen on Substrate, and Evaluation

Albumen allergen was immobilized on the Substrate 21 obtained in (3) of Example 7, in the same manner as in (1) of Example 8 to obtain a biochip. In the same manner as in (2) and (3) of Example 8, the resulting biochip was subjected to fluorescence measurement after contact with the albumen allergy-positive human serum. The results are shown in Table 3.

Comparative Example 5

Biochip Comprising Albumen Allergen Immobilized on NHS-Esterified PMMA Substrate (Substrate 1)

Albumen allergen was immobilized on the Substrate 1 obtained in (2) of Example 1, in the same manner as in (1) of Example 8 to obtain a biochip. In the same manner as in (2) and (3) of Example 8, the resulting biochip was subjected to fluorescence measurement after contact with the albumen allergy-positive human serum. The results are shown in Table 3.

Comparative Example 6

Biochip Comprising Albumen Allergen Immobilized on Polyallylamine-Bound PMMA Substrate (Substrate 14)

Albumen allergen was immobilized on the Substrate 14 obtained in (1) of Comparative Example 3, in the same manner as in (1) of Example 8 to obtain a biochip. In the same manner as in (2) and (3) of Example 8, the resulting biochip was subjected to fluorescence measurement after contact with the albumen allergy-positive human serum. The results are shown in Table 3.

TABLE 3

| | Substrate | Polymer type | Unit ratio (m/(m + n)) | Signal value | Noise value | SN ratio |
|---|---|---|---|---|---|---|
| Example 8 | Substrate 3 | Partially methoxycarbonyl-modified Polyallylamme | 30 mol % | 10131 | 173 | 58.7 |
| | Substrate 4 | | 50 mol % | 10960 | 268 | 40.9 |
| | Substrate 5 | | 70 mol % | 11127 | 375 | 29.6 |
| Example 9 | Substrate 22 | Partially ethoxycarbonyl-modified Polyallylamine | 30 mol % | 11850 | 164 | 72.2 |
| | Substrate 23 | | 50 mol % | 10903 | 178 | 61.3 |
| | Substrate 24 | | 70 mol % | 8549 | 187 | 45.8 |
| Example 10 | Substrate 25 | Partially propyloxycarbonyl-modified polyallylamine | 30 mol % | 9591 | 145 | 66.1 |
| | Substrate 26 | | 50 mol % | 10500 | 169 | 62.1 |
| | Substrate 27 | | 70 mol % | 10272 | 205 | 50.1 |
| Example 11 | Substrate 17 | Partially propanamide-modified polyallylamine | 50 mol % | 11221 | 376 | 29.8 |
| Example 12 | Substrate 19 | Partially N,N-dimethy 1 propanamide-modified polyallylamine | 50 mol % | 10981 | 178 | 61.6 |
| Example 13 | Substrate 20 | Partially N,N-diethy 1 propanamide-modified polyallylamine | 50 mol % | 8813 | 311 | 28.3 |
| Example 14 | Substrate 21 | Partially N-isopropy 1 propanamide-modified polyallylamine | 50 mol % | 11221 | 316 | 35.5 |
| Comparative Example 5 | Substrate 1 | None | — | 4304 | 966 | 4.5 |
| Comparative Example 6 | Substrate 14 | Poly allylamine | — | 7972 | 1074 | 7.4 |

Table 3 shows the fluorescence value (signal value) of the part on which albumen allergen was immobilized, the fluorescence value (noise value) of the part on which albumen allergen was not immobilized, and the ratio of the signal value to the noise value (SN ratio), in the substrate brought into contact with the albumen allergy-positive human serum and the dye-labeled anti-human IgE goat polyclonal antibody. The fluorescence detected herein is derived from the dye-labeled anti-human IgE goat polyclonal antibody. The larger the binding amount of the dye-labeled anti-human IgE goat polyclonal antibody, the higher the value. The signal value corresponds to the amount of dye-labeled anti-human IgE goat polyclonal antibody bound to the complex of the human IgE antibody (measurement target substance) and the albumen allergen (selective-binding substance). On the other hand, the noise value corresponds to the amount of dye-labeled anti-human IgE goat polyclonal antibody non-specifically bound to the substrate. The value of the SN ratio increases as the amount of dye-labeled anti-human IgE goat polyclonal antibody bound to the complex increases, and as the amount of dye-labeled anti-human IgE goat polyclonal antibody non-specifically bound to the substrate decreases. The SN ratio was therefore used as an index of the detection sensitivity of the biochip.

The substrates on which the partially methoxycarbonyl-modified polyallylamine obtained by modification of side-chain amino groups of polyallylamine was bound (Example 8, Substrates 3 to 5) showed higher SN ratios compared to the substrate on which no polymer was bound (Comparative Example 5, Substrate 1), and even compared to the substrate on which polyallylamine was bound (Comparative Example 6, Substrate 14). This is assumed to be due to the effect of suppression of non-specific adsorption of the dye-labeled anti-human IgE goat polyclonal antibody, which causes an increase in the noise value, by the modification with the methoxycarbonyl group; and due to improvement of the efficiency of formation of the complex, by the control of the density of reactive functional groups on the substrate surface.

We also found the same effect for the substrates on which the partially ethoxycarbonyl-modified polyallylamine was bound (Example 9, Substrates 22 to 24), the substrates on which the partially propyloxycarbonyl-modified polyallylamine was bound (Example 10, Substrates 25 to 27), the substrate on which the partially propanamide-modified polyallylamine was bound (Example 11, Substrate17), the substrate on which the partially N,N-dimethylpropanamide-modified polyallylamine was bound (Example 12, Substrate19), the substrate on which the partially N,N-diethylpropanamide-modified polyallylamine was bound (Example 13, Substrate20), and the substrate on which the partially N-isopropylpropanamide-modified polyallylamine was bound (Example 14, Substrate21). Since the SN ratio varied depending on the type of the functional group for the modification of the polymer, we found that the type of the functional group for the modification of the polymer is important to obtain a biochip excellent in both the signal value and the SN ratio.

INDUSTRIAL APPLICABILITY

We provide a biochip capable of highly sensitively detecting a measurement target substance. By using the biochip, more accurate identification of molecules and diagnosis are possible.

The invention claimed is:

1. A biochip comprising a selective-binding substance capable of selectively binding to a measurement target substance, the selective-binding substance being immobilized on a surface of a substrate through a polymer containing a unit represented by Formula (Ia) or (Ib):

(Ia)

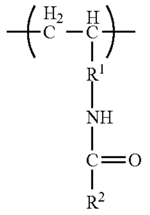

(Ib)

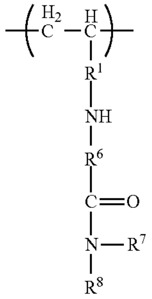

wherein, in Formulae (Ia) and (Ib), $R^1$ represents $C_1$-$C_4$ alkylene; $R^2$ represents $R^3$, $OR^4$, or $NHR^5$; $R^3$ represents a hydrogen atom or $C_1$-$C_4$ alkyl; $R^4$ represents $C_1$-$C_4$ alkyl; $R^5$ represents $C_1$-$C_4$ alkyl; $R^6$ represents $C_1$-$C_2$ alkylene; and $R^7$ and $R^8$ each independently represent a hydrogen atom or $C_1$-$C_4$ alkyl.

2. The biochip according to claim 1, wherein the polymer is represented by the Formula (Ia).

3. The biochip according to claim 1, wherein the polymer is a heteropolymer.

4. The biochip according to claim 3, wherein the heteropolymer is a heteropolymer comprising a unit represented by Formula (II):

(II)

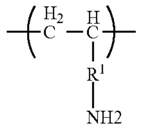

wherein $R^1$ represents $C_1$-$C_4$ alkylene.

5. The biochip according to claim 1, wherein the polymer has a number average molecular weight of 300 g/mol to 1,000,000 g/mol.

6. The biochip according to claim 1, wherein the selective-binding substance is a nucleic acid or a protein.

7. A method of detecting a measurement target substance using the biochip according to claim 1, the biochip comprising a selective-binding substance capable of selectively binding to the measurement target substance, the selective-binding substance being immobilized on a surface of a substrate, the method comprising:

bringing a specimen containing the measurement target substance into contact with the surface of the substrate, to thereby form a complex with the selective-binding substance; and detecting the complex.

8. A biochip comprising a selective-binding substance capable of selectively binding to a measurement target substance, the selective-binding substance being immobilized on a surface of a substrate through a polymer containing a unit represented by (Ib):

(Ib)

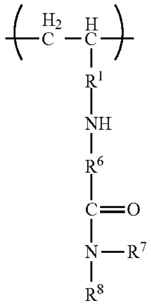

wherein, in (Ib), $R^1$ represents $C_1$-$C_4$ alkylene; $R^2$ represents $R^3$, $OR^4$, or $NHR^5$; $R^3$ and $R^5$ each independently represents a hydrogen atom or $C_1$-$C_4$ alkyl; $R^4$ represents $C_1$-$C_4$ alkyl; $R^6$ represents $C_1$-$C_2$ alkylene; and $R^7$ and $R^8$ each independently represent a hydrogen atom or $C_1$-$C_4$ alkyl.

* * * * *